(12) United States Patent
Mandecki (10) Patent No.: US 6,387,623 B1
(45) Date of Patent: May 14, 2002

(54) SCREENING OF DRUGS FROM CHEMICAL COMBINATORIAL LIBRARIES EMPLOYING TRANSPONDERS

(75) Inventor: Wlodek Mandecki, Libertyville, IL (US)

(73) Assignee: Pharmaseq, Monmouth Junction, NJ (US)

( * ) Notice: Subject to any disclaimer, the term of this patent is extended or adjusted under 35 U.S.C. 154(b) by 0 days.

(21) Appl. No.: 09/537,620

(22) Filed: Mar. 29, 2000

Related U.S. Application Data (63) Continuation of application No. 08/908,222, filed on Aug. 7, 1997, which is a continuation of application No. 08/564,945, filed on Nov. 30, 1995, now abandoned.

(51) Int. Cl.$^7$ .......................... C12Q 1/68; G01N 33/53
(52) U.S. Cl. ........................................... 435/6; 435/7.1
(58) Field of Search ............................. 435/6, 91.2, 7.1

(56) References Cited

U.S. PATENT DOCUMENTS

| | | |
|---|---|---|
| 4,177,253 A | 12/1979 | Davies et al. |
| 4,297,337 A | 10/1981 | Mansfield et al. |
| 4,452,773 A | 6/1984 | Molday |
| 4,454,234 A | 6/1984 | Czerlinski |
| 4,556,883 A | 12/1985 | Strietzel |
| 4,672,040 A | 6/1987 | Josephson |
| 4,777,145 A | 10/1988 | Luotola et al. |
| 4,778,769 A | 10/1988 | Forrest et al. |
| 4,822,566 A | 4/1989 | Newman |
| 4,857,893 A | 8/1989 | Carroll |
| 4,923,819 A | 5/1990 | Fernandez et al. |
| 4,941,201 A | 7/1990 | Davis |
| 4,965,188 A | 10/1990 | Mullis et al. |
| 5,019,815 A | 5/1991 | Lemelson et al. |
| 5,034,192 A | 7/1991 | Wrighton et al. |
| 5,071,774 A | 12/1991 | Vorpahl et al. |
| 5,153,583 A | 10/1992 | Murdoch |
| 5,200,051 A | 4/1993 | Cozzette et al. |
| 5,202,231 A | 4/1993 | Drmanac et al. |
| 5,214,409 A | 5/1993 | Beigel |
| 5,218,343 A | 6/1993 | Stobbe et al. |
| 5,223,851 A | 6/1993 | Hadden et al. |
| 5,235,326 A | 8/1993 | Beigel et al. |
| 5,245,332 A | 9/1993 | Katzenstein |
| 5,250,944 A | 10/1993 | Urbas et al. |
| 5,252,962 A | 10/1993 | Urbas et al. |
| 5,257,011 A | 10/1993 | Beigel |
| 5,262,772 A | 11/1993 | Urbas et al. |
| 5,266,926 A | 11/1993 | Beigel |
| 5,284,748 A | 2/1994 | Mroczkowski et al. |
| 5,347,263 A | 9/1994 | Carroll et al. |
| 5,422,636 A | 6/1995 | Urbas et al. |
| 5,440,300 A | 8/1995 | Spillman, Jr. |
| 5,445,970 A | 8/1995 | Rohr |
| 5,466,348 A | 11/1995 | Holm-Kennedy |
| 5,481,262 A | 1/1996 | Urbas et al. |
| 5,491,097 A | 2/1996 | Ribi et al. |
| 5,492,806 A | 2/1996 | Drmanac et al. |
| 5,525,464 A | 6/1996 | Drmanac et al. |
| 5,552,270 A | 9/1996 | Khrapko et al. |
| 5,641,634 A | 6/1997 | Mandecki |
| 5,736,332 A | 4/1998 | Mandecki |
| 5,741,462 A | 4/1998 | Nova et al. |
| 5,751,629 A | 5/1998 | Nova et al. |
| 5,770,455 A | 6/1998 | Cargill et al. |
| 5,874,214 A | 2/1999 | Nova et al. |
| 5,925,562 A | 7/1999 | Nova et al. |
| 5,961,923 A | 10/1999 | Nova et al. |
| 5,972,639 A | 10/1999 | Parandoosh |
| 6,017,496 A | 1/2000 | Nova et al. |
| 6,025,129 A | 2/2000 | Nova et al. |

FOREIGN PATENT DOCUMENTS

| | | |
|---|---|---|
| EP | 0526173 A2 | 2/1993 |
| WO | WO90/13666 | 11/1990 |
| WO | WO93/04199 | 3/1993 |
| WO | WO93/21340 | 10/1993 |
| WO | WO96/36436 | 11/1996 |
| WO | WO97/19958 | 6/1997 |
| WO | WO97/20073 | 6/1997 |
| WO | WO97/20074 | 6/1997 |

OTHER PUBLICATIONS

Gingeras TR et al. "Hybridization properties of immobilized nucleic acids" *Nucleic Acids Research* (1987) vol. 15, No. 13.

Hooft van Hujisdujnen, RAM et al. "A means to reduce the complexity of oligonucleotides encoding degenerate peptides" *Nucleic Acids Research* (1992) vol. 20, No. 4.

Hultman et al. "Direct solid phase sequencing of genomic DNA using magnetic beads as solid support" *Nucleic Acids Research* (1989) vol. 17, No. 13, pp. 4937–4946.

Ihalainen et al. *Biotechniques* (1994) vol. 16, pp. 938–943.

Kurstak, E. *Enzyme Immunodiagnostics* (1986) pp. 13–22, Academic Press, NY.

Lam, KS et al. "A new type of synthetic peptide library for identifying ligand–binding activity" *Nature* (Nov. 7, 1991) vol. 354, pp. 82–84.

Maskos, E. et al. "Oligonucleotide hybridisations [sic] on glass supports: a novel linker for oligonucleotide synthesis and hybridisation [sic] properties of oligonucleotides synthesized in situ" *Nucleic Acids Research* (1992) vol. 20, No. 7, pp. 1679–1684.

(List continued on next page.)

Primary Examiner—Eggerton A. Campbell
(74) Attorney, Agent, or Firm—Brinks Hofer Gilson & Lione (57) ABSTRACT

Materials and methods are disclosed for identifying chemical compounds having desired binding properties towards a binding partner of pharmaceutical interest. The method employs transponders associated with the solid phase material used in the assay and a scanner to encode and decode data stored electronically on the transponder. The data stored on the transponder identifies the monomeric building blocks added during the synthesis. The structural identification of synthesized compounds bound to the solid phase is done by decoding the transponder.

25 Claims, 9 Drawing Sheets

OTHER PUBLICATIONS

McHugh, T. "Flow Microsphere Immunoassay for the Quantitative and Simultaneous Detection of Multiple Soluble Analytes" *Methods in Cell Biology* (1990) vol. 42, pp. 575–595.

Mirzabekov, AD. "DNA sequencing by hybridization—a megasequencing method and a diagnostic tool" *Tibtech* (1994) vol. 12.

Moran et al. "Radio frequency tag encoded combinatorial library method for the discovery of tripeptide–substituted cinnamic acid inhibitors of the protein tyrosine phosphatase PTP1B" *J. Am. Chem Soc.* (1995) vol. 117, pp. 10787–10788.

Morrissey, NE et al. "Modified method for determining carcinoembryonic antigen in the presence of human anti–murine antibodies" *Clinical Chemistry* (1993) vol. 39, No. 3.

Nicolaou et al. "Radiofrequency encoded combinatorial chemistry" *Angew. Chem Int. Ed.* (1995), vol. 34, No. 210, pp. 2289–2291.

Pease, AC et al. "Light–generated oligonucleotide arrays for rapid DNA sequence analysis" *Proc. Natl. Acad. Sci.* (1994), vol. 91, pp. 5022–5026.

Pierce catalog. (1994) pp. T159, T314–T315, Rockford, Illinois US.

*Principles And Practice Of Immunoassay*, Chapter 5, "Immunoassay Design And Optimization".

*Principles And Practice Of Immunoassay*, Chapter 13, "Heterogeneous Fluoroimmunoassay."

Sambrook et al. *Molecular Cloning: A laboratory manual* (1989) $2^{nd}$ ed. Lake Press, NY.

Service, R. "Radio tags speed compound synthesis" *Science*, (Oct. 27, 1995) vol. 270, p. 577.

Sproat, BS and DM Brown "A new linkage for solid phase synthesis of oligodeoxyribonucleotides" *Nucleic Acids Research* (1985) vol. 13, pp. 2979–2987.

Urdea et al. "A comparison of non–radioisotopic hybridization assay methods using fluorescent, chemiluminescent and enzyme labeled synthetic oligodeoxyribonucleotide probes" *Nucleic Acids Research*, (1988) vol. 16, No. 11 pp. 4937–4956

Albretsen, C et al. "Applications of magnetic beads with covalently attached oligonucleotides in hybridization: Isolation and detection of specific measles virus mRNA from a crude cell lysate" *Analytical Biochemistry* (1990) vol. 189, pp. 40–50.

Alper, J. "Drug Discovery on the assembly line" *Science* (Jun. 3, 1994) vol. 264, pp. 1399–1401.

Atkinson, T et al. "A convenient procedure for the synthesis of oligodeoxyribonucleotide affinity columns for the isolation of mRNA" *Nucleic Acids Research*, (1988), vol. 16, No. 13.

Cargill, JF and BE Toyonaga. *The Chemical Factory: An Assembly Line Approach to Automated Combinatorial Chemistry on Solid Phase.*

Caruthers, MH et al. "Deoxyoligonucleotide synthesis via the phosphoramidite method" *Gene Amplification and Analysis*, vol. III, (TS Papas et al., eds.) Elsevier Press, Amsterdam.

Drmanac, R et al. "DNA sequence determination by hybridization: a strategy for efficient large–scale sequencing." *Science* (1993) vol. 260, pp. 1649–1652.

Flore, F et al. "The Abbott IMx Automated Benchtop Immunochemistry Analyzer System" *Clinical Chemistry* (1998) vol. 34, No. 9.

Ghosh, SS and GF Musso. "Covalent attachment of oligonucleotides to solid supports" *Nucleic Acids Research*, (1987) vol. 15, No. 13.

SCREENING OF DRUGS FROM CHEMICAL COMBINATORIAL LIBRARIES EMPLOYING TRANSPONDERS

This appln is a cont of Ser. No. 08/908,222 filed Aug. 7, 1997 which is a cont of Ser. No. 08/564,945 filed Nov. 30, 1995, abn.

BACKGROUND OF THE INVENTION

This invention relates to materials and methods for screening chemical compounds for potential pharmaceutical activity, and more specifically to an electronically-indexed solid phase assay using transponders embedded in the solid phase particles.

Methods of solid-phase chemical synthesis have been widely used in drug discovery. Their advantages include the ease of separating compounds synthesized on the solid phase from the substrates and byproducts of the reactions by centrifugation, filtration, magnetic separation, gravity and others, and the ease of handling and assaying the compounds after the synthesis. Compounds immobilized on the solid phase can be subjected readily to a variety of assays, including immunoassays.

Many classes of compounds have been successfully synthesized using solid-phase methods, including peptides, oligonucleotides and small molecules. There are two general types of compounds that can be synthesized in a combinatorial fashion, linear polymers consisting of one or more monomeric building blocks, e.g. peptides, and compounds built on a small-molecule scaffold. In the latter case the structure of the molecule with regard to the position of the building block can be considered "branched." The latter case is exemplified by compounds from the benzadiazepine family. Hybrid approaches are also possible, where the compounds have a branched structure, but each branch is composed of a linear chain of building blocks, or vice versa.

In existing solid-phase chemical synthesis methods the solid phase is a passive vehicle. The main utility of the solid phase is to aid in separating the desired product or intermediate of the reaction from the substrate and byproducts.

Conventional methods for identification of the synthesized compound are limited because the amount of the compound needed for full characterization (often 1 mg) is much more than the quantity that can be released from a single solid phase particle. One way to overcome this problem is to tag the particle with a biomolecule during the course of the synthesis by co-synthesizing this biomolecule together with the compound of interest. Examples include the co-synthesis of a nucleic acid for peptide combinatorial libraries, the use of halogenated derivatives of carboxylic acids, or the co-synthesis of peptides as tags for small molecules. This method also has limitations, however, in that the chemistry of the synthesis of small molecules may be incompatible with the chemistry of molecular encoding. Additionally, using a molecular tag can double the number of synthetic steps involved in the process.

SUMMARY OF THE INVENTION

This invention overcomes many of these problems by employing transponders embedded in the particles used as the solid phase. Thus, each individual solid phase particle can be assigned a unique index number, electronically encoded inside the particle, that can be recovered at will at any time after the synthesis is complete, thus enabling the identification of the compound on the bead.

According to the present invention, the solid phase performs an additional function, i.e. storage of the information about the progress of the chemical synthesis in an electronic memory element inside the solid-phase particle, or bead. The contents of the memory can be retrieved by a dedicated scanner device at a desired time after the synthesis is completed, or at multiple times during the synthesis, or monitored continuously during an assay. In the combinatorial chemical synthesis methods of this invention, the solid-phase particles are derivatized with a chemical scaffold, or support, on which synthetic condensations are conducted.

Following combinatorial synthesis, the pool of derivatized particles can be exposed to a target protein of pharmaceutical interest to investigate which particles carry compounds that bind to the target protein, using immunoassay techniques. The particle can also be a source of a small quantity of the compound of interest for identification purposes. The identified compounds can be re-synthesized and subjected to further phases of drug development.

In one aspect, the present invention provides a particle for use in solid phase chemical synthesis, wherein a transponder is embedded in the particle.

In a second aspect, the present invention provides methods of solid phase chemical synthesis employing an electronically indexed solid phase.

DETAILED DESCRIPTION OF THE INVENTION

Figure 1:
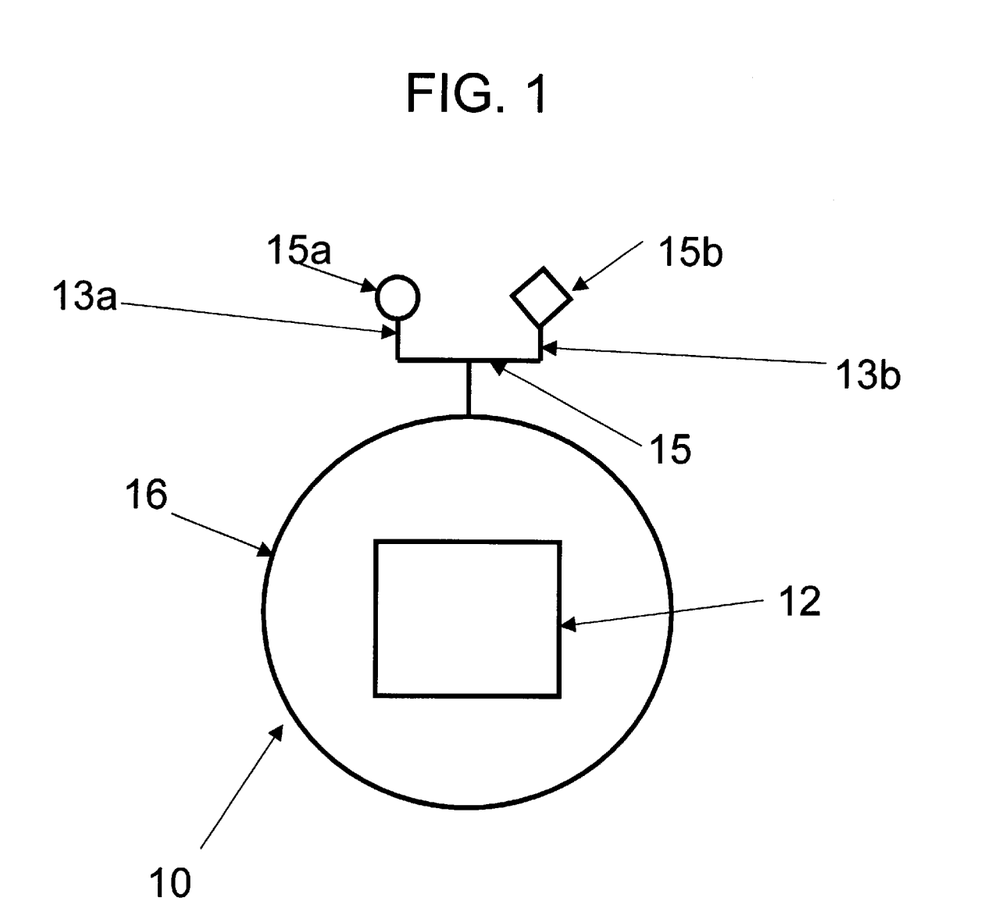
FIG. 1 is a schematic depiction of a solid phase particle having a transponder and a carrying a molecular scaffold for combinatorial synthesis.

FIG. 1 depicts an electronically indexed solid phase particle having a transponder for use in combinatorial synthesis on a molecular scaffold. The particle 10 has a transponder 12, and a surface 16 of the particle 10 is derivatized to display a small molecule scaffold 15 having active groups 13a, 13b initially protected with protecting groups 15a, 15b. Active groups 13a, 13b become the condensation points after deprotection.

Scaffolds for the combinatorial synthesis of small molecules that have been implemented in the art include benzadiazepines, hydantoins, quinolones, alkynes, alkenes, benzoisothiazolones, amides, ureas, tetrahydrofurans, biaryls and others. The scaffold typically contains two to four active groups, that are orthogonally protected, but that can be selectively deprotected and subjected to condensations involving a set of low-molecular weight chemicals, often of similar chemical reactivity.

According to principles of combinatorial chemistry, after the particles are derivatized, the scaffold is deprotected at the first reactive group, and the particles are divided into groups, the number of groups being equal to the number of condensations to be done in parallel. The groups of particles undergo chemical coupling, each group with a different coupling reagent. The particles are then mixed thoroughly, the second reactive group is deprotected, and the particles are again divided into groups to undergo the second coupling step. The procedure is repeated until condensations on all active groups of the scaffold are completed.

Figure 1A:
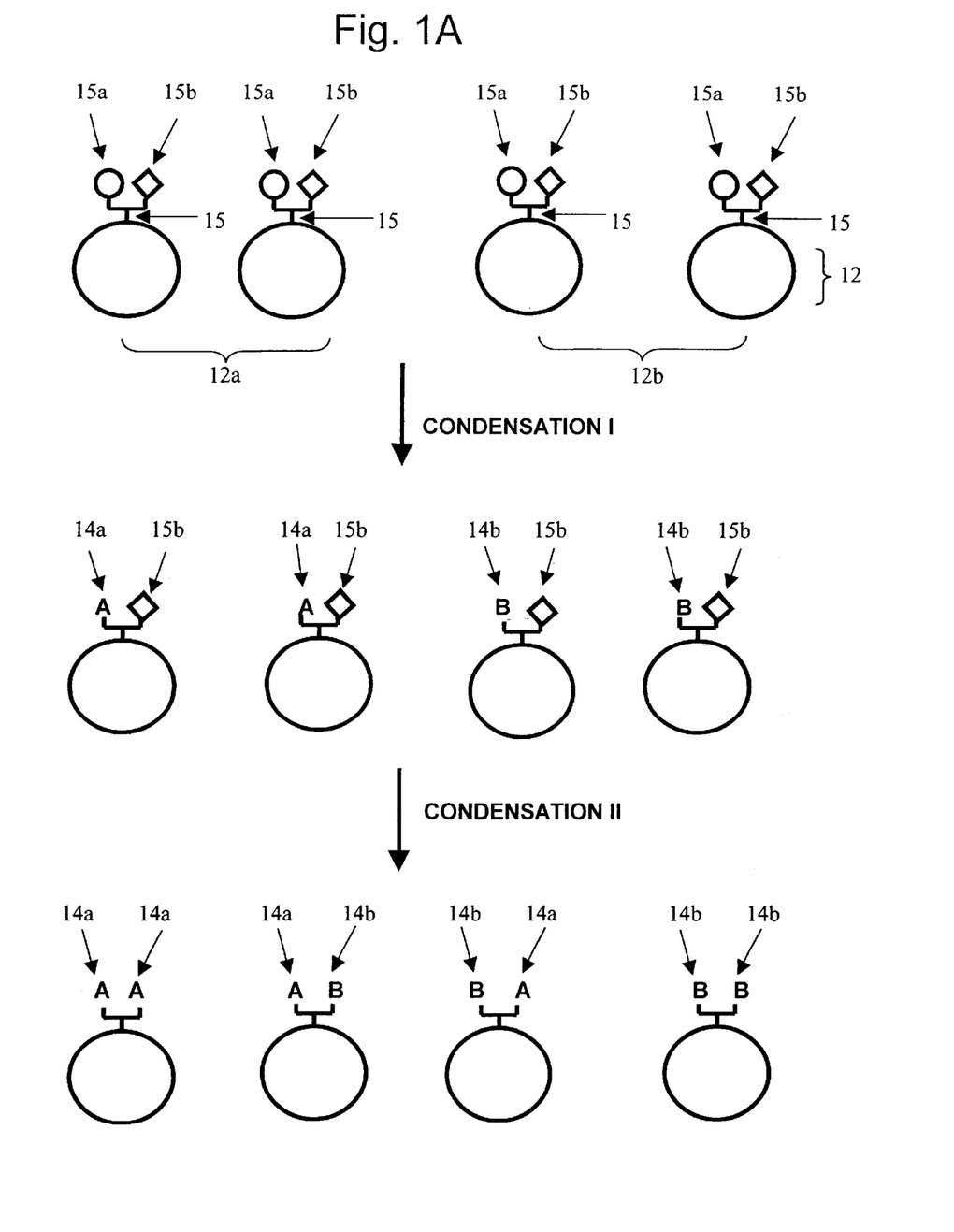
FIG. 1A is a schematic depiction of a combinatorial synthesis procedure of this invention.

In FIG. 1A, a set of transponders 12 is split into groups 12a, 12b, the number of groups being equal to the number of different synthetic building blocks 14a, 14b. The groups of transponders 12a, 12b are electronically encoded with a scanner device (not shown) with an alphanumeric character identifying the first building block to be condensed on the support. The protecting group 15a is removed and the groups of transponders 12a, 12b are subjected to a condensations with the building blocks 14a, 14b. Often, the condensations are done in parallel. The protecting group 15b is removed, the second cycle of encoding and synthesis takes place, and the process continues for as long as desired or practical. After the final condensation the scaffold is not cleaved from the support.

Figure 2:
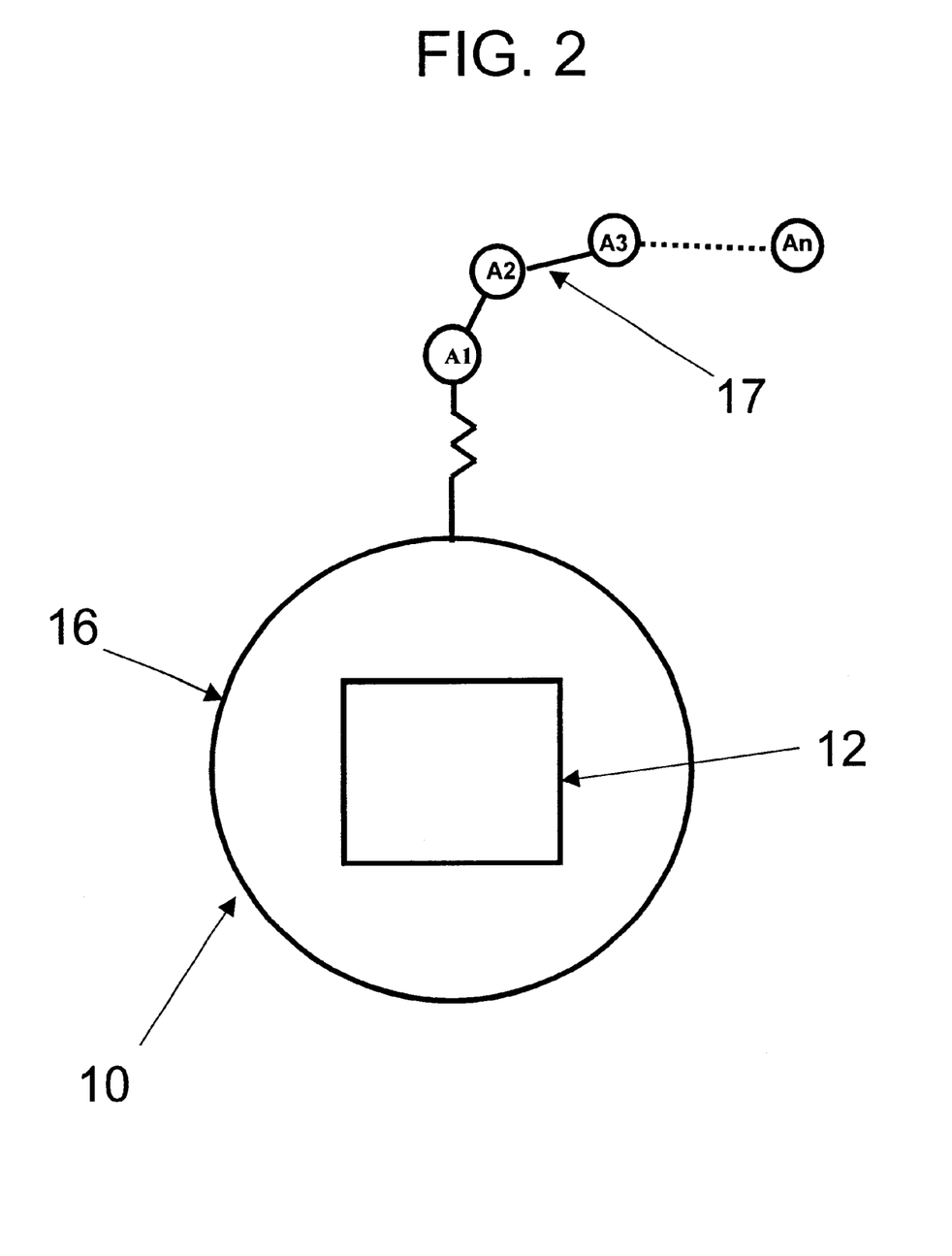
FIG. 2 is a schematic depiction of a solid phase particle containing a transponder for use in solid phase combinatorial synthesis.

FIG. 2 depicts a solid phase particle 10 of the present invention, having a transponder 12 embedded in the particle 10 and a peptide 17 attached to the outer surface 16 of the particle 10.

A transponder is a radio transmitter-receiver activated for transmission of data by reception of a predetermined signal. The signal comes from a dedicated scanner that also receives and processes the data sent by the transponder in response to the signal. The scanner can also be used to perform the "write" function, i.e., the process of encoding the data on the transponder. Such a combination instrument is referred to as a scanner read/write device. An advantage of the transponder-scanner system is that the two units are not electrically connected by wire, but instead are coupled inductively, i.e. by the use of electromagnetic radiation, typically in the range from 5–1,000 kHz, but also up to 1 GHz and higher.

Figure 3:
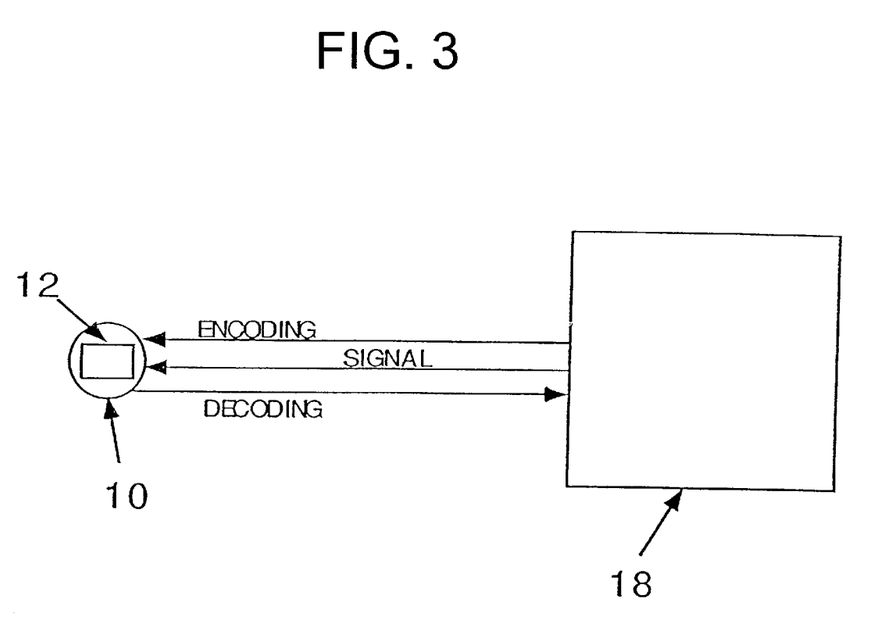
FIG. 3 is a schematic diagram of the signal pathway for encoding and encoding data on the transponders embedded in the solid phase.

FIG. 3 is a flow chart illustrating the communication between the transponder 12 and a remote scanner read/write device 18. The transponder 12 embedded in the solid phase beads 10 is encoded with data sent by electromagnetic waves from a remote scanner read/write device 18. After the assay steps are completed, the beads 10 are analyzed to detect the presence of a label indicative of binding of analyte and those that show the presence of the label are decoded. The scanner 18 sends a signal to the transponder 12. In response to the signal, the transponder 12 transmits the encoded data to the scanner 18.

The transponders must be programmable to allow the user to independently encode index numbers in the same number or a larger number of independent electronic memory fields as the number of condensation cycles. The encoding process at any particular cycle should not change or erase the encoding done in the previous cycles. Accordingly, it is necessary to shield non-target transponders from the electromagnetic radiation emitted by the scanner device, as by a metal barrier, or other means.

Some transponders similar to the Bio Medic Data Systems Inc. (BMDS, 255 West Spring Valley Ave., Maywood, N.J.) manufactures a programmable transponder for use in laboratory animal identification. The transponder is implanted in the body of an animal, such as a mouse. The transponder is glass-encapsulated to protect the electronics inside the transponder from the environment. One of the transponders manufactured by this corporation, model# IPTT-100, has dimensions of 14×2.2×2.2 mm and weighs 120 mg. The transponder is user-programmable with up to 16 alphanumeric characters, the 16th letter programmable independently of the other 15 letters, and has a built-in temperature sensor as well. The electronic animal monitoring system (ELAMS) includes also a scanner read/write system, such as the DAS-5001 console system, to encode or read data on/from the transponder. The construction of the transponder and scanner is described in U.S. Pat. Nos. 5,250,944, 5,252,962, and 5,262,772, the disclosures of which are incorporated herein by reference. Other similar transponder-scanner systems include the multi-memory electronic identification tag (U.S. Pat. No. 5,257,011) manufactured by AVID Corporation (Norco, Calif.) and a system made by TEMIC-Telefunken (Eching, Germany). AVID's transponder has dimensions of 1 mm×1 mm×11 mm, and can encode 96 bits of information, programmable by the user. The present invention can be practiced with different transponders, which might be of different dimensions and have different electronic memory capacity. The BMDS transponder fulfills the minimum programmability requirements for suitability for combinatorial synthesis.

The commercially available transponders are relatively large in size. The speed at which the transponders may be decoded is limited by the carrier frequency and the method of transmitting the data. In typical signal transmission schemes, the data are encoded by modulating either the amplitude, frequency or phase of the carrier. Depending on the modulation method chosen, compression schemes, transmission environment, noise and other factors, the rate of the signal transmission is within two orders of magnitude of the carrier frequency. For example, a carrier frequency of 1,000 Hz corresponds to rates of 10 to 100,000 bits per second (bps). At the rate of 10,000 bps the transmission of 100 bits will take 0.01 sec. The carrier frequency can be several orders of magnitude higher than 1,000 hz, so the transmission rates can be proportionally higher as well.

Therefore, the limiting factor in the screening process is the speed at which the transport mechanism carries the transponders through the read window of the fluorometer/scanner device. The rate of movement of small particles or cells is $10^4$–$10^5$ per second in state-of-the-art flow cytometers. A flow cytometer may be used to practice the present invention, if two conditions are met: (1) the transponders are small enough to pass through the flow chamber, and (2) the design of the flow chamber of the flow cytometer is modified to include an antenna for collecting the electromagnetic radiation emitted by transponders.

Figure 4:
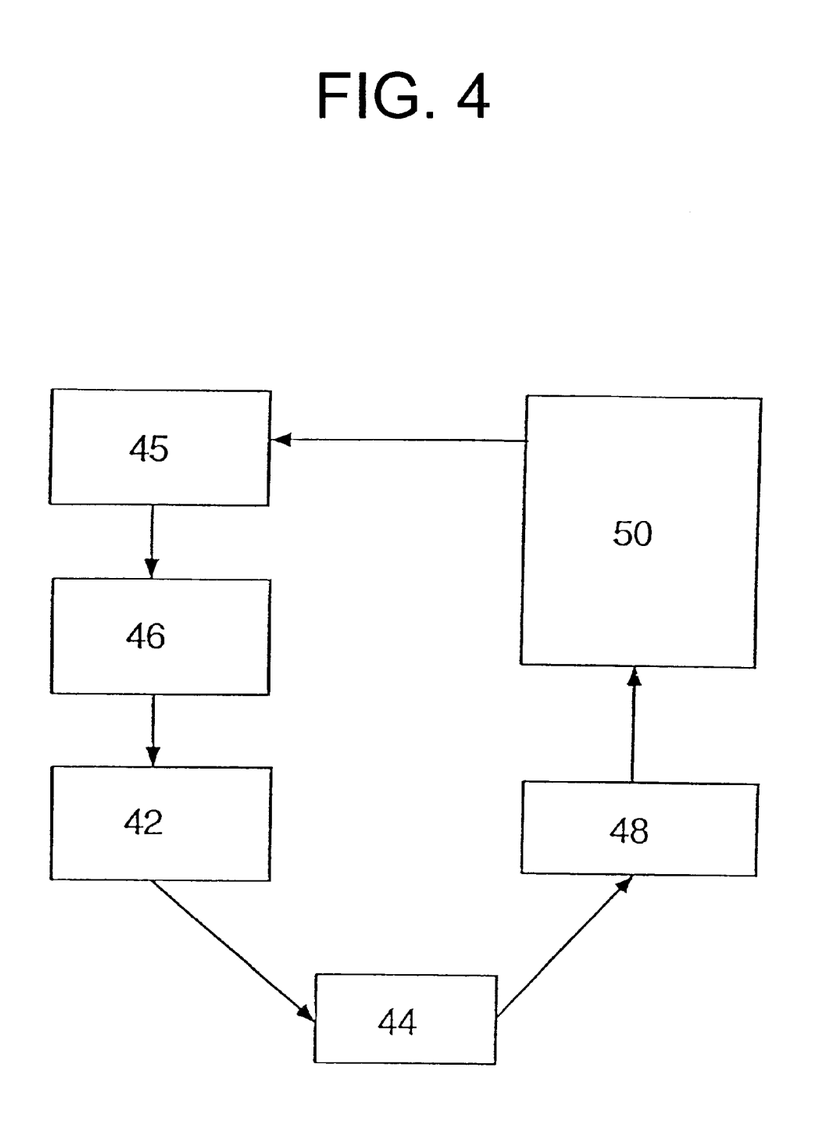
FIG. 4 is a schematic representation of a miniature transponder.
Figure 5:
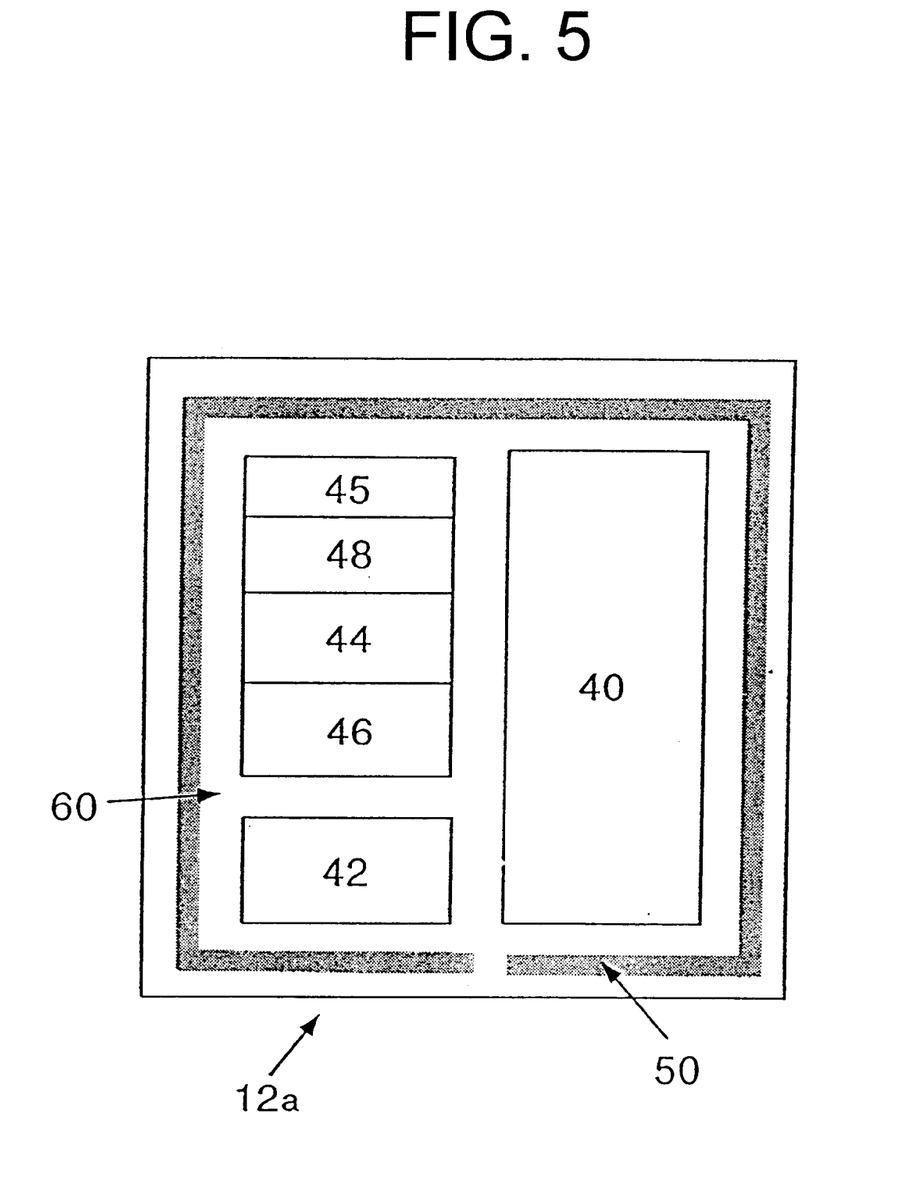
FIG. 5 is a plan view of a miniature transponder.

A miniature transponder is depicted in FIGS. 4 and 5. The source of the electrical power for the transponder 12a is at least one photovoltaic cell 40 within the transponder 12a, illuminated by light, preferably from a laser (not shown). The same light also induces the fluorescence of the fluorogenic molecules immobilized on the surface of the transponder 12a. The transponder 12a includes a memory element 42 that may be of the EEPROM type. The contents of the memory is converted from the digital form to the analog form by a Digital-to-Analog converter 44 mounted on the transponder 12a. The signal is amplified by an amplifier 46, mixed with the carrier signal produced by an oscillator 48, and emitted to the outside of the transponder 12a by an antenna 50.

The contents of the transponder memory can be permanently encoded during the manufacturing process of the transponder, different batches of transponders being differently encoded. Preferably, the memory of the transponder is user-programmable, and is encoded by the user just before, during, or just after the biological material is deposited on the surface of the transponder. A user-programmable transponder 12a must have the "write" feature enabled by the antenna 50, amplifier 44 and the Analog-to-Digital converter 46 manufactured on the transponder 12a, as well as the dedicated scanner read/write device.

The advantages of this transponder are several-fold. First, the dimension of the transponder is reduced, since most of the volume of current transponders is occupied by the solenoid. The design discussed above will enable the production of cubic transponders on the order of 0.01 to 1.0 mm as measured along a side of the cube, preferably 0.05 to 0.2 mm.

Second, a large number of transponders can be manufactured on a single silicon wafer, and no further assembly would be required to attach the solenoid to the VLSI chip. As depicted schematically in FIG. 6, a silicon wafer 60 is simply cut to yield active transponders 12a. Third, the transponder, according the new design, will not need the glass capsule as an enclosure, further reducing the size of the transponder. Silicone dioxide ($SiO_2$) would constitute a significant portion of the surface of the transponder, and $SiO_2$, has chemical properties which are very similar to glass in terms of the feasibility of derivatization or immobilization of biomolecules. Fourth, and perhaps most importantly, the narrow focus of the beam of the laser light would enable only one transponder to be active at a time, significantly reducing the noise level. Advanced user-programmability is desirable as well, various memory registers need to be addressable independently (writing in one register should not erase the contents of other registers).

A second preferred embodiment of the present invention comprises a method for the combinatorial synthesis of branched compounds on a scaffold linked to an electronically indexed solid phase. The starting material is a scaffold molecule with several active groups, initially protected with orthogonal protecting groups, immobilized on the transponders through a molecular linker. The first active group is deprotected, and the transponders are divided into groups at random, the number of groups being equal to the number of building blocks. The transponders are electronically encoded with an alphanumeric character unequivocally identifying the first building block to be condensed on the support. Because the building block added to the scaffold will be different for each group, the encoded character is also different for each group of transponders. The groups of transponders are then subjected to condensations with the building blocks, often in parallel. The groups of transponders are combined and mixed thoroughly, the second active group on the scaffold now carrying the first building block is now deprotected, and the transponders are again divided into group at random. The second cycle of encoding and synthesis is performed, and the process is repeated as many times as desired or practical, but only until all active groups on the scaffold have undergone coupling. After the final condensation the scaffold remains on the transponders.

Figure 6:
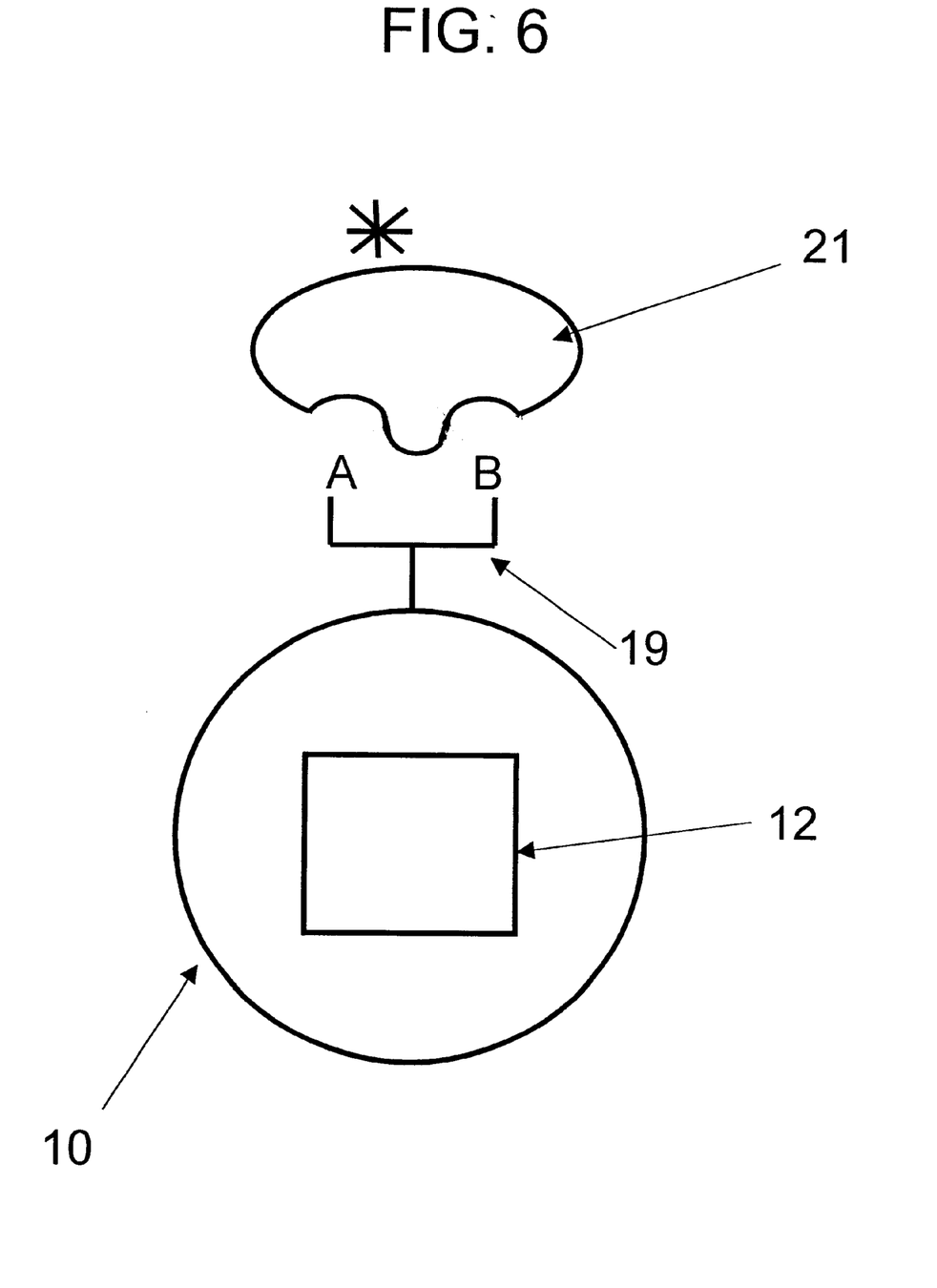
FIG. 6 is a schematic diagram of a procedure for screening synthesized compounds for binding to biomolecular targets of pharmaceutical interest.

FIG. 6 depicts the analysis of the synthesized compounds bound to transponders. The particles 10 carrying synthesized compounds 19 are subsequently incubated with a labelled biomolecular target 21 of pharmaceutical interest, e.g., a receptor molecule, in a single vessel (not shown) in a standard immunoassay. The label may be fluorescent, colorimetric, radioactivity or the like. After analyzing the transponders to detect the label, the transponders are decoded to determine the structure of the synthesized compound attached to the transponders.

The chemical libraries synthesized on transponders can be subjected to screening for binding to several types of biomolecular targets of pharmaceutical interest, such as proteins and peptides, and their covalently modified forms, protein or peptide conjugates, small molecules (haptens), ribonucleic acid (RNA), modified nucleic acids and analogs of nucleic acids (in particular protein-nucleic acids, PNAs).

The target can be a complex of biomolecules, such as a virus particle, a protein-nucleic acid complex, or a protein-hapten complex. The target can be a cell, in such case the relevant molecules that participate in binding process during the assay are typically cell surface receptors or other elements of the cell wall or membrane. The target may be present in a variety of forms, such as a solution in a simple buffer, but also in a complex biological fluid, such as blood, serum, urine, saliva, and many others.

After incubation with the target, the transponders are analyzed to detect the label, and the electronic memory of the transponder is decoded using a dedicated scanner. The two measurements can be done at the same time manually. Alternatively, a single automated instrument can perform both functions. Such an instrument can be a modified fluorometer in which the scanner is mounted in the proximity of the readout window, and the reading of fluorescence and the decoding of the memory of the transponder are coordinated by a central computer.

Figure 7:
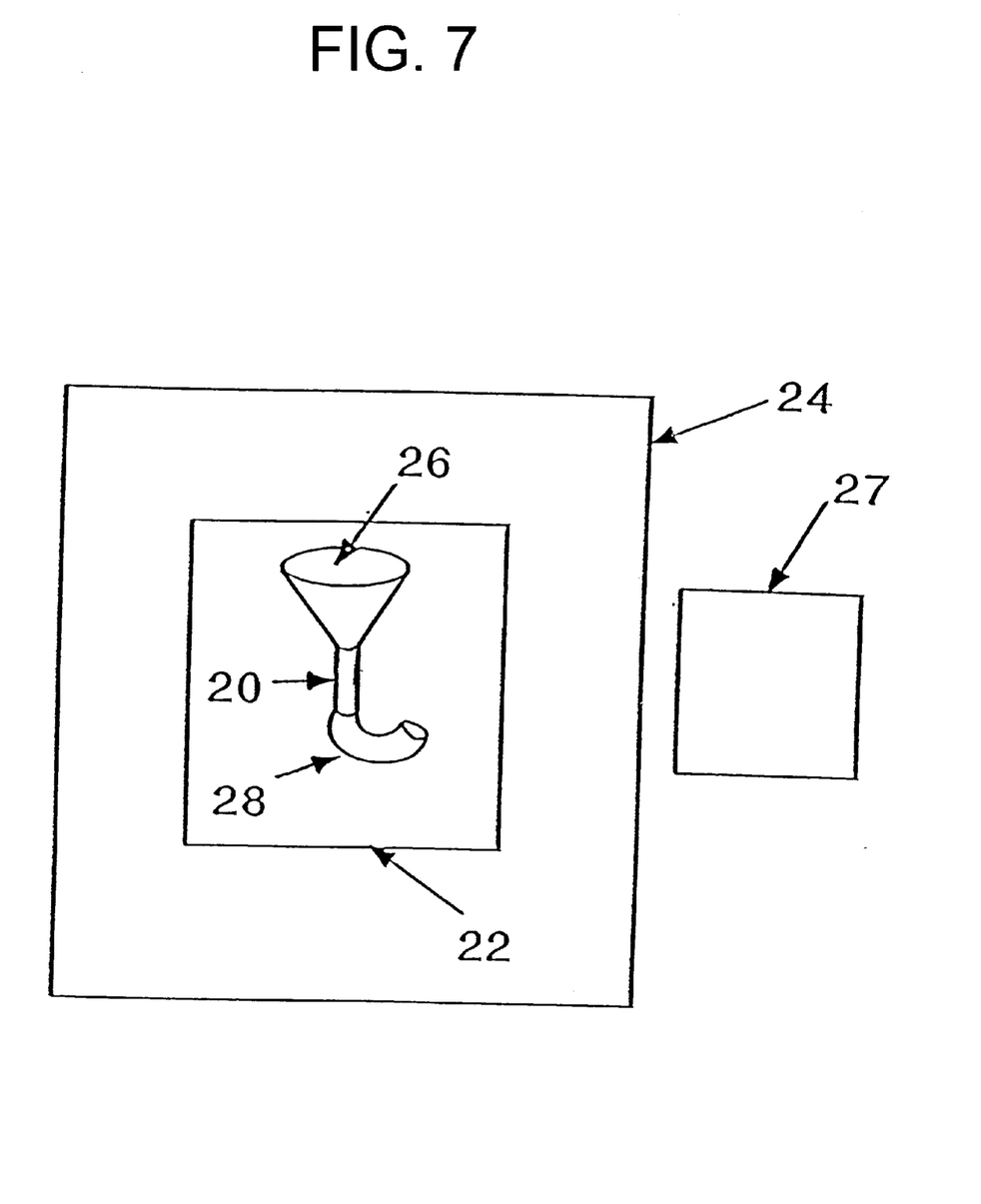
FIG. 7 is a plan view of a transport system and analytical instrument for implementing this invention.

FIG. 7 shows the analytical instrumentation and transport system used in an embodiment of the present invention. A quartz tube 20 is mounted in the readout window 22 of a fluorometer 24. The quartz tube 20 is connected to a metal funnel 26. The length of the quartz tube 20 is similar to the dimensions of the transponder 12. Transponders 12 are fed into the metal funnel 26, and pass from the funnel 26 into the quartz tube 20, where the fluorescence is read by the fluorometer 24 and the transponder 12 is decoded by the scanner 27, and then exit through a metal tube 28 and are conducted to a collection vessel (not shown). The metal funnel 26 and metal tube 28 are made of metal shield transponders 12 outside of the read window 22 by shielding the electromagnetic signal from the scanner 27. This shielding prevents the scanner signal from reaching more than one transponder 12, causing multiple transponders 12 to be decoded.

Minimal modification of the fluorometer 24 would be needed in the vicinity of the location that the tube occupies at the readout moment to allow for positioning of the transponder reading device. To assure compatibility with existing assays, the glass surrounding the transponder could be coated with plastic currently used to manufacture beads.

Figure 8:
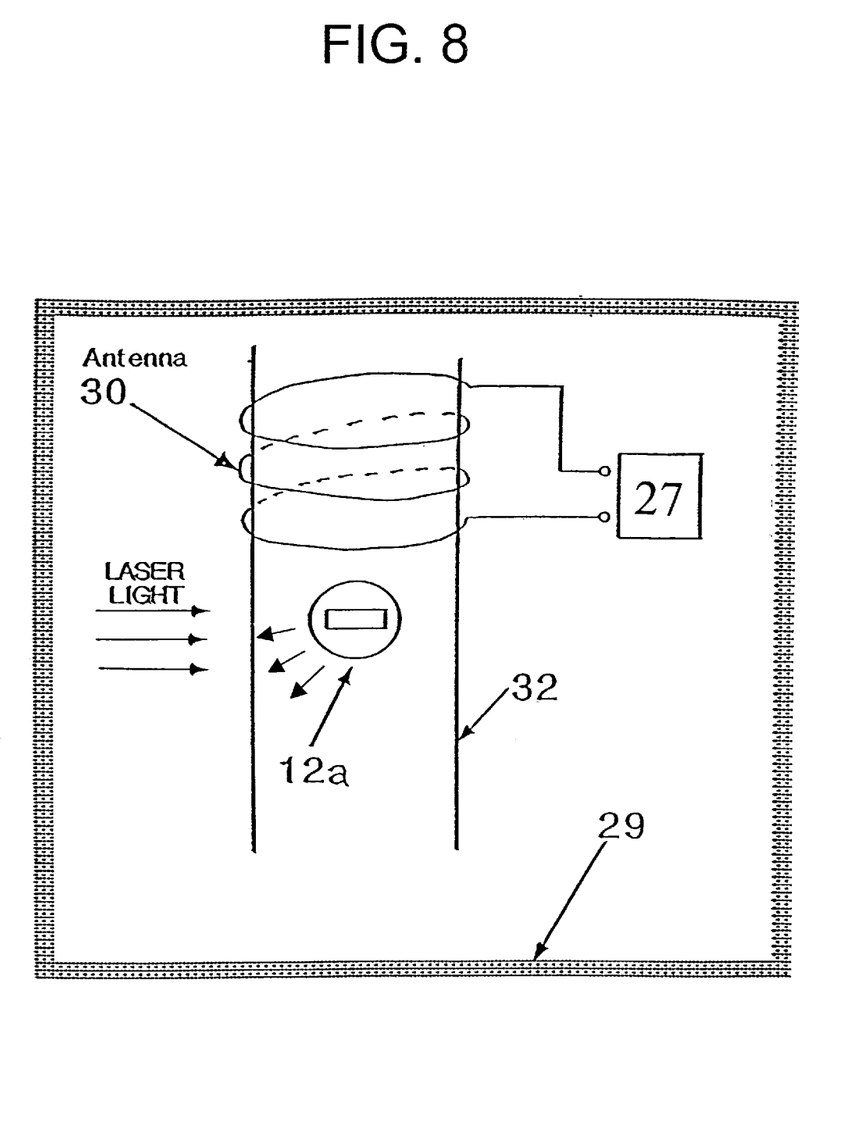
FIG. 8 is a plan view of a modified flow cytometer for high speed analysis of solid phase particles of this invention.

In a preferred design, depicted in FIG. 8, a metal coil antenna 30 is wrapped around the flow cell 32 of a flow cytometer 29. The transponders 12 pass through the flow cell 32, and are decoded by the scanner device 27. The signal carrying the data sent from the transponders 12 is amplified by a first amplifier 34 and processed by the scanning device 27. As the transponders 12 are decoded, fluorescence from the transponders 12 is detected and analyzed by the flow cytometer 29.

EXAMPLE 1

Synthesis Of Combinatorial Library of Peptides On Transponders

A set of 200 transponders, model IPTT-100, manufactured by BMDS is used in this example. The outside glass surface of the transponders is derivatized by treatment with aminoalkylsilane as follows. First, the transponders are cleaned by washing with xylene, followed by a 70% ethanol rinse and air drying. Then, the transponders are submerged for about 30 seconds in a 2% solution of aminopropyltriethoxysilane (Cat.# A3648, Sigma, St. Louis, Mo.) in dry acetone. The transponders are then sequentially are rinsed with dry acetone and distilled water, and air dried.

This procedure is described in the, Pierce catalog (pp. T314–T315 of the 1994 catalog, Pierce, Rockford, Ill.). The aminoalkylsilane treatment results in covalent linkage of the primary amine group to the surface of the transponder.

Peptide synthesis is carried out on the solid support created by aminoalkylsilane treatment, using an Applied Biosystems peptide synthesizer model 431A at a 1 mM scale using standard Fmoc chemistry. The 200 derivatized transponders are divided into 5 groups of 40 transponders, and are inserted into 55 ml reaction vessels. The volume of transponders in each group is about 2 ml.

First, a six-residue peptide linker, common to all five groups, is synthesized, corresponding to the following sequence: $NH_2$-Met-Phe-Gly-Cys-Ser-Gly. Second, each group undergoes a single coupling reaction, to join one residue to the growing polymer. Specifically, the following residues are added:

Group 1: Ala
Group 2: Arg
Group 3: Asp
Group 4: Gly
Group 5: Ser

Following these condensations, the transponders are removed from the reaction vessels and each transponder of each group is assigned an index number indicating the residue added in the first condensation reaction. The transponders are then pooled in a common vessel, mixed thoroughly, and again divided into five groups of forty transponders. The groups again undergo a single condensation, as above, and the transponders are again encoded with a second index number identifying the residue added in the second coupling step. Finally, five coupling reactions, common to all 200 transponders, are carried out to add the following sequence: $NH_2$-Ser-Gly-Ser-Cys-Arg.

The results of the synthesis should provide all 25 possible combinations of Ala, Arg, Asp, Gly and Ser at the 7 and 8 positions, as shown below:

Ala Ala
Arg Arg
$NH_2$-Ser-Gly-Ser-Cys-Arg-Asp-Asp-Met-Phe-Gly-Cys-Ser-T
Gly Gly
Ser Ser where T represents the transponder surface. The transponders are then removed from the reaction vessels, pooled and deprotected using standard methods. The peptides are not cleaved from the transponders because no labile bond is present. The peptides are oxidized by incubating the transponders in 10 mM ammonium acetate pH 8.5 overnight at room temperature with gentle stirring, are then rinsed and stored in phosphate-buffered saline.

The synthesized peptide library is screened against platelet glycoprotein IIb/III, a mediator of aggregation of platelets through binding of fibrinogen. The IIb/III protein is radio-labelled with $^{125}I$. The 200 transponders carrying the peptide library are submerged in a solution of $^{125}I$-labelled IIb/III protein in phosphate-buffered saline (PBS), and incubated at room temperature for 2 hours. The volume of the solution is sufficient to immerse the transponders. The transponders are rinsed five times with PBS. The transponders are then analyzed to detect the label radioactivity, and the transponders are decoded to yield the structure of the synthesized peptide bound thereto.

I claim:

1. A method of screening a compound for binding to a target biomolecule of pharmaceutical interest, comprising the steps of:
    (a) providing a solid phase having a transponder associated with the solid phase and the compound attached to a surface of the solid phase, wherein the transponder comprises of memory elements containing data indicating the identity of the compound, a radio-frequency transmitter and one or more photovoltaic cells providing a source of electrical power for the transponder when illuminated by light;
    (b) providing a fluorescently labeled form of the target biomolecule;
    (c) incubating the solid phase having the compound attached thereto with the fluorescently labeled biomolecule;
    (d) analyzing the solid phase using the light to detect any fluorescently labeled target biomolecule directly or indirectly attached to the compound; and
    (e) decoding the transponder memory elements to determine the identity of the compound.

2. The method of claim 1, wherein the compound is a peptide.

3. The method of claim 1, wherein the compound is a small organic molecule.

4. The method of claim 1, wherein the solid phase comprises a surface of the transponder.

5. The method of claim 1, wherein one or more layers of coating are deposited on an outer surface of the transponder and the compound is attached to a coating layer.

6. The method of claim 5, wherein the layers of coating comprise of glass, latex or plastic.

7. The method of claim 1, wherein the solid phase is particulate.

8. A method of screening a compound for binding to a target biomolecule of pharmaceutical interest, comprising the steps of:
    (a) providing a solid phase having a transponder associated with the solid phase and having a chemical scaffold attached to a surface of the solid phase, the scaffold having active groups, and the transponder comprising of memory elements, a radio-frequency transmitter and one or more photovoltaic cells providing a source of electrical power for the transponder when illuminated by light;
    (b) sequentially adding chemical substituents to the active groups on the scaffold to synthesize the compound;
    (c) encoding data on the transponder memory elements to indicate each substituent added;
    (d) providing a fluorescently labeled form of the target biomolecule;
    (e) incubating the solid phase having the compound attached thereto with the fluorescently labeled biomolecule;
    (f) analyzing the solid phase using the light to detect any fluorescently labeled target biomolecule directly or indirectly attached to the compound; and
    (g) decoding the transponder memory elements to determine the identity of the synthesized compound.

9. The method of claim 8, wherein the solid phase comprises a surface of the transponder.

10. The method of claim 8, wherein one or more layers of coating are deposited on an outer surface of the transponder and the compound is attached to a coating layer.

11. The method of claim 10, wherein the layers of coating comprise of glass, latex or plastic.

12. The method of claim 8, wherein the solid phase is particulate.

13. A method of screening a compound for binding to a target biomolecule of pharmaceutical interest, comprising the steps of:

(a) providing a solid phase having a transponder associated with the solid phase and having a chemical scaffold attached to a surface of the solid phase, the scaffold having active groups, and the transponder comprising of memory elements containing an unique identifier, a radio-frequency transmitter and one or more photovoltaic cells providing a source of electrical power for the transponder when illuminated by light;

(b) sequentially adding chemical substituents to the active groups on the scaffold to synthesize the compound;

(c) associating the unique identifier with the identity of the chemical substituents;

(d) providing a fluorescently labeled form of the target biomolecule;

(e) incubating the solid phase having the compound attached thereto with the fluorescently labeled biomolecule;

(f) analyzing the solid phase using the light to detect any fluorescently labeled target biomolecule directly or indirectly attached to the compound; and (g) decoding the transponder memory elements to determine the identity of the synthesized compound.

14. The method of claim 13, wherein the solid phase comprises a surface of the transponder.

15. The method of claim 13, wherein one or more layers of coating are deposited on an outer surface of the transponder and the compound is attached to a coating layer.

16. The method of claim 15, wherein the layers of coating comprise of glass, latex or plastic.

17. The method of claim 13, wherein the solid phase is particulate.

18. A method of screening compounds for binding to a target biomolecule of pharmaceutical interest, comprising the steps of:

(a) providing a particulate solid phase having a transponder associated with each particle and a chemical scaffold having active groups attached to a surface of the particle, wherein the transponder comprises of memory elements, a radio-frequency transmitter and one or more photovoltaic cells providing a source of electrical power for the transponder when illuminated by light;

(b) dividing the particles randomly into groups;

(c) sequentially adding chemical substituents to the active groups on the scaffold to synthesize the compounds, encoding data on the transponder for each addition to indicate the substituent added, combining the groups and redividing the particles into groups after each addition;

(d) repeating the addition, combining and re-dividing steps until all active groups on the scaffold have been reacted;

(e) providing a fluorescently labeled form of the target biomolecule;

(f) incubating the particles having the synthesized compounds attached thereto with the fluorescently labeled target biomolecule;

(g) analyzing the particles using the light to detect any fluorescently labeled target biomolecule directly or indirectly attached to the compounds; and (h) decoding the transponder memory elements to determine the identity of the synthesized compounds on the particles analyzed.

19. The method of claim 18, wherein the solid phase comprises a surface of the transponder.

20. The method of claim 18, wherein one or more layers of coating are deposited on an outer surface of the transponder and the compound is attached to a coating layer.

21. The method of claim 20, wherein the layers of coating comprise of glass, latex or plastic.

22. A method of screening compounds for binding to a target biomolecule of pharmaceutical interest, comprising the steps of:

(a) providing a particulate solid phase having a transponder associated with each particle and a chemical scaffold having active groups attached to a surface of the particle, wherein the transponder comprises of memory elements containing an unique identifier, a radio-frequency transmitter and one or more photovoltaic cells providing a source of electrical power for the transponder when illuminated by light;

(b) dividing the particles randomly into groups;

(c) sequentially adding chemical substituents to the active groups on the scaffold to synthesize the compounds, combining the groups and re-dividing the particles into groups after each addition;

(d) repeating the addition, combining and re-dividing steps until all active groups on the scaffold have been reacted;

(e) associating the unique identifiers with the identity of the chemical substituents;

(f) providing a fluorescently labeled form of the target biomolecule;

(g) incubating the particles having the synthesized compounds attached thereto with the fluorescently labeled target biomolecule;

(h) analyzing the particles using the light to detect any fluorescently labeled target biomolecule directly or indirectly attached to the compounds; and (i) decoding the unique identifiers in the transponder memory elements to determine the identity of the synthesized compounds on the particle analyzed.

23. The method of claim 22, wherein the solid phase comprises a surface of the transponder.

24. The method of claim 22, wherein one or more layers of coating are deposited on an outer surface of the transponder and the compound is attached to a coating layer.

25. The method of claim 24, wherein the layers of coating comprise of glass, latex or plastics.

* * * * *

UNITED STATES PATENT AND TRADEMARK OFFICE
CERTIFICATE OF CORRECTION

PATENT NO.    : 6,387,623 B1
DATED         : May 14, 2002
INVENTOR(S)   : Wlodeck Mandecki It is certified that error appears in the above-identified patent and that said Letters Patent is hereby corrected as shown below:

<u>Column 10,</u>
Line 60, delete "plastics" and substitute -- plastic -- in its place.

Signed and Sealed this

Eleventh Day of March, 2003

JAMES E. ROGAN
*Director of the United States Patent and Trademark Office*